(12) United States Patent
Lawrenson et al.

(10) Patent No.: US 10,679,745 B2
(45) Date of Patent: Jun. 9, 2020

(54) SYSTEM AND METHOD FOR PROVIDING A PATIENT WITH PERSONALIZED ADVICE

(71) Applicant: KONINKLIJKE PHILIPS N.V., Eindhoven (NL)

(72) Inventors: Matthew John Lawrenson, Bussigny-Pres-de-Lausanne (CH); Julian Charles Nolan, Pully (CH)

(73) Assignee: Koninklijke Philips N.V., Eindhoven (NL)

( * ) Notice: Subject to any disclaimer, the term of this patent is extended or adjusted under 35 U.S.C. 154(b) by 781 days.

(21) Appl. No.: 15/324,878

(22) PCT Filed: Jun. 24, 2015

(86) PCT No.: PCT/EP2015/064172
§ 371 (c)(1),
(2) Date: Jan. 9, 2017

(87) PCT Pub. No.: WO2016/005186
PCT Pub. Date: Jan. 14, 2016

(65) Prior Publication Data
US 2017/0203071 A1    Jul. 20, 2017

(30) Foreign Application Priority Data
Jul. 10, 2014 (EP) .................................. 14176465

(51) Int. Cl.
*A61M 16/00* (2006.01)
*A61M 16/06* (2006.01)
(Continued)

(52) U.S. Cl.
CPC ........ *G16H 40/63* (2018.01); *A61M 16/0057* (2013.01); *A61M 16/0683* (2013.01);
(Continued)

(58) Field of Classification Search
CPC .......... A61M 16/0605; A61M 16/0616; A61M 16/0633; A61M 16/0683;
(Continued)

(56) References Cited

U.S. PATENT DOCUMENTS 7,376,700 B1    5/2008  Clark
7,827,038 B2    11/2010 Richard
(Continued)

FOREIGN PATENT DOCUMENTS

JP          2010131091 A    6/2010
WO      WO2011073814 A1    6/2011
(Continued)

*Primary Examiner* — Tu A Vo
(74) *Attorney, Agent, or Firm* — Michael W. Haas

(57) ABSTRACT

The present invention relates to an apparatus (10) for providing a patient (12) with personalized advice (56) relating to a use of a patient interface (18) for providing a flow of breathable gas and/or to a use of a pressure support system (14) including such a patient interface (18), the apparatus (10) including: a receiving unit (32) for receiving (i) a virtual model of at least a part of a head of the patient (12), (ii) technical data relating to a technical design and functionality of the patient interface (18) and/or of the pressure support system (14), and (iii) usage data including information on how the patient (12) is using the patient interface (18) and/or the pressure support system (14); and an advice unit (36) for generating the personalized advice (56) on how to improve the use of the patient interface (18) and/or of the pressure support system (14) based on the virtual model, the technical data and the usage data.

14 Claims, 4 Drawing Sheets

(51) Int. Cl.
*G16H 40/63* (2018.01)
*G06F 19/00* (2018.01)
*G06T 7/00* (2017.01)
*G09B 5/02* (2006.01)
*G16H 50/50* (2018.01)

(52) U.S. Cl.
CPC ............ *G06F 19/00* (2013.01); *G06T 7/0014* (2013.01); *G09B 5/02* (2013.01); *A61M 16/06* (2013.01); *A61M 2205/13* (2013.01); *A61M 2205/332* (2013.01); *A61M 2205/3331* (2013.01); *A61M 2205/3375* (2013.01); *A61M 2205/502* (2013.01); *A61M 2205/58* (2013.01); *A61M 2205/581* (2013.01); *A61M 2205/583* (2013.01); *A61M 2230/62* (2013.01); *G06F 19/321* (2013.01); *G06F 19/3481* (2013.01); *G06T 2207/30088* (2013.01); *G16H 50/50* (2018.01)

(58) Field of Classification Search
CPC ........... A61M 2205/0227; A61M 16/06–0655; A61M 2016/0661; A61M 2210/0606; A61M 2210/0618; A61M 2205/332; A61M 2205/3306; A61M 2205/13; A61M 16/0057; A61M 2230/62; A61M 2205/581; A61M 2205/3331; A61M 2205/58; A61M 2205/502; A61M 2205/3375; A42B 1/00; A62B 18/00; A62B 18/02; A62B 18/04; A62B 18/08; A62B 18/084; A62B 18/025; A62B 18/06; G16H 40/63; G16H 50/50; G06T 7/0014; G06T 2207/30088; G09B 5/02
See application file for complete search history.

(56) References Cited

U.S. PATENT DOCUMENTS

| | | | |
|---|---|---|---|
| 7,827,039 | B2 | 11/2010 | Butcher |
| 2004/0133604 | A1* | 7/2004 | Lordo ................... A61M 16/06 |
| 2004/0267565 | A1 | 12/2004 | Grube |
| 2006/0023228 | A1* | 2/2006 | Geng ..................... A61B 5/411 356/601 |
| 2008/0060652 | A1* | 3/2008 | Selvarajan ............ A61M 16/06 128/206.21 |
| 2008/0078396 | A1* | 4/2008 | Janbakhsh ............ A61M 16/06 128/205.25 |
| 2008/0306767 | A1 | 12/2008 | Bodlaender |
| 2011/0220112 | A1 | 9/2011 | Connor |
| 2012/0232403 | A1* | 9/2012 | Smith .................... A61B 5/015 600/474 |
| 2012/0240933 | A1* | 9/2012 | Haas ..................... A61M 16/06 128/204.21 |
| 2013/0014012 | A1 | 1/2013 | Boucher |
| 2013/0263857 | A1 | 10/2013 | Ahmad |
| 2013/0339039 | A1 | 12/2013 | Roman |
| 2014/0278319 | A1* | 9/2014 | Thiruvengada ..... G06F 17/5009 703/11 |
| 2015/0193650 | A1* | 7/2015 | Ho ........................ A61M 16/06 382/128 |

FOREIGN PATENT DOCUMENTS

| | | |
|---|---|---|
| WO | WO2012048100 A2 | 4/2012 |
| WO | WO2013183038 A2 | 12/2013 |
| WO | WO2014009914 A2 | 1/2014 |

* cited by examiner

SYSTEM AND METHOD FOR PROVIDING A PATIENT WITH PERSONALIZED ADVICE

CROSS-REFERENCE TO RELATED APPLICATIONS

This patent application claims the priority benefit under 35 U.S.C. § 371 of international patent application no. PCT/EP2015/064172, filed Jun. 24, 2015, which claims the benefit of European Application No. EP14176465.4 filed Jul. 10, 2014. These applications are hereby incorporated by reference herein.

FIELD OF THE INVENTION

The present invention relates to a system for providing a patient with personalized advice relating to a use of a patient interface for providing a flow of breathable gas and/or to a use of a pressure support system comprising such a patient interface. The present invention further relates to a corresponding method for providing a patient with personalized advice. Still further, the present invention relates to a computer program for carrying out said method.

BACKGROUND OF THE INVENTION

Patient interfaces, such as masks for covering the mouth and/or nose, are used for delivering gas to a patient. Such gases, like air, cleaned air (oxygen, or any modification of the latter), are submitted to the patient via the patient interface in a pressurized or unpressurized way. The patient interface is usually provided as a part of a pressure support system that comprises besides the patient interface a pressure generator for generating the flow of breathable gas. Usually, this pressure generator is fluidly connected to the patient interface via one or more conduits acting as gas conducting hoses.

For several chronic disorders and diseases, a long-term attachment of such a patient interface to a patient is necessary or at least advisable.

One non-limiting example for such a disease is obstructive sleep apnea or obstructive sleep apnea syndrome (OSA). OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by a reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring. Another exemplary disease which is usually treated in a similar manner by means of a patient interface is chronic obstructive pulmonary disease (COPD).

Different invasive and non-invasive treatments for OSA and COPD are known. One of the most powerful non-invasive treatments is the usage of Continuous Positive Airway Pressure (CPAP) or Bi-Positive Airway Pressure (BiPAP) in which a patient is connected to a pressure generator via a patient circuit including one or more tubes, wherein the pressure generator blows pressurized gas into the patient interface and into the patient's airway in order to keep it open. Positive air pressure is thus provided to the patient by means of the patient interface that is worn by the patient typically during sleep. The typical design of a PAP apparatus comprises a floor or table mounted therapy device which includes the pressure generator.

Examples of the above-mentioned patient interfaces are:
nasal masks, which fit over the nose and delivery gas to the nasal passages,
oral masks, which fit over the mouth and deliver gas to the mouth,
full-face masks, which fit over both the nose and the mouth and deliver gas to both, and
nasal pillows, which are regarded as patient interfaces as well within the scope of the present invention and which consist of nasal inserts that deliver gas directly to the nasal passages.

Due to the complexity of the pressure support system including such patient interfaces many users often have problems with correctly operating the pressure support system and with correctly attaching the patient interface when using them the first time. Inexperienced users who begin the treatment are confronted with a completely new apparatus to master and a completely new terminology to understand. This can cause confusion and increases the likelihood of non-compliance to the PAP therapy care plan. However, not only inexperienced users have problems to correctly operate a PAP therapy device. Some aspects of using the PAP apparatus are complex even if understood. For example, the correct placement of the patient interface may involve the movement and tightening/untightening of several straps of a headgear that is used for donning the patient interface to the patient's head. These straps have to be attached and tightened in a specific order in order to achieve an adequate seal and comfort that is necessary for an effective PAP therapy. This can be a fiddly operation. On the other hand, each patient has to attach the patient interface in a different manner, meaning e.g. that the straps have to be tightened for every patient differently due to the individual size and shape of the head and face of each patient.

Patients, especially inexperienced patients, thus need advice and instructions how to use the pressure support system and/or the patient interface in a proper way. Currently, these instructions and advices are included in instruction manuals, video tutorials, or the patient directly receives such advices from the physician and/sleep practitioner. This means, however, that the advice on how to use the pressure support system and/or the patient interface correctly is a single instance (a book, a pdf document, a web page, a video etc.) distributed to many users. While the information included in such books, pdf documents, web pages or videos may contain advice on how to adapt for different head shapes and circumstances, it is not truly personalized to a specific user. These general manuals are also not personalized to the current setup or configuration of the PAP apparatus and the patient interface. Typically, current forms of advice manuals do not adapt to current usage, for example if a user performs action A frequently, perhaps more than an average user, then the manual does not adapt to give advice specifically for a user with such a usage profile. Where personal advice is given to a user, e.g. by a physician, it is not provided in-situ.

US 2013/0014012 A1 discloses a system and method for providing an interactive electronic technical manual. This system and method allow the user to interact with the manual (e.g. select what information to be displayed etc.), but do not personalize the information to both a user, for example to the level of using the user's own head dimensions, and the current state/configuration of apparatus.

WO 2011/073814 A1 discloses a pressure support system including a patient interface for delivering a pressurized flow of breathable gas to a patient, the system being configured to provide information to a user position, fit or seal between the subject and the patient interface. Such information may include, for example, a location on the patient interface at which the integrity of the seal is compromised, adjustments that could be made by the subject to enhance the interface between the patient interface and the subject, different types and/or sizes of patient interfaces that could be used to enhance the fit and seal between the system and the subject, and/or other information.

U.S. Pat. No. 7,827,038 B2 discloses a mask fitting system for selecting a mask system for a patient by comparing 3-D scan data of the patient with mask system data including data of a plurality of masks and being stored in a mask system database, so as to generate a best-fit mask system result. The best-fit result may include one or more mask system recommendations for the patient.

Thus, there is still room for improvement.

SUMMARY OF THE INVENTION

It is an object of the present invention to provide a system and a method which provide the patient with personalized advice relating to the usage of a patient interface and/or a pressure support system including such a patient interface. It is particularly an object to provide a system and method that enable generating an interactive manual giving the patient personalized advice and considering individual head shapes and sizes as well as considering the current setup of the patient interface. The system and method shall be capable of generating personalized advices including information on how the patient may improve the usage of the patient interface and/or the pressure support system.

According to an aspect of the present invention, a system for providing a patient with personalized advice relating to a use of a patient interface for providing a flow of breathable gas and/or to a use of a pressure support system comprising such a patient interface is provided, wherein the system comprises:

a receiving unit for receiving (i) a virtual model of at least a part of a head of the patient, (ii) technical data relating to a technical design and functionality of the patient interface and/or of the pressure support system, and (iii) usage data including information on how the patient is currently using the patient interface and/or the pressure support system; and an advice unit for generating the personalized advice on how to improve the current use of the patient interface and/or of the pressure support system based on the virtual model, the technical data and the usage data.

According to a further aspect of the present invention, the system may further comprise a pressure support system including (i) a pressure generator for generating a flow of breathable gas and (ii) a patient interface for providing the flow of breathable gas to the patient.

According to a further aspect of the present invention, a corresponding method is provided which comprises the steps of receiving (i) a virtual model of at least a part of a head of the patient, (ii) technical data relating to a technical design and functionality of the patient interface and/or of the pressure support system, and (iii) usage data including information on how the patient is currently using the patient interface and/or the pressure support system; and generating the personalized advice on how to improve the current use of the patient interface and/or of the pressure support system based on the virtual model, the technical data and the usage data.

According to a further aspect of the present invention, a computer program is provided which comprises program code means for causing a computer to carry out the steps of the above-mentioned method when said computer program is carried out on a computer.

According to a further aspect of the present invention, a system for providing a patient with personalized advice relating to a use of a patient interface for providing a flow of breathable gas and/or to a use of a pressure support system comprising such a patient interface is presented, wherein the system comprises a processor and a computer-readable storage medium, wherein the computer readable storage medium contains instructions for execution by the processor, wherein the instructions cause the processor to perform the steps of:

receiving a virtual model of at least a part of a head of a patient, receiving technical data relating to a technical design and functionality of the patient interface and/or of the pressure support system, receiving usage data including information on how the patient is currently using the patient interface and/or the pressure support system, and generating the personalized advice on how to improve the current use of the patient interface and/or of the pressure support system based on the virtual model, the technical data and the usage data.

Preferred embodiments of the invention are defined in the dependent claims. It shall be understood that the claimed method as well as the claimed computer program have similar and/or identical preferred embodiments as the claimed system and as defined in the dependent claims.

The term "personalized advice" shall refer to instructions including explanations for the patient how he/she may improve the current use of the patient interface and/or the current use of the pressure support system. These advices may include information presented to the patient in written, audible or tactile form. The advices so to say give the user a kind of interactive manual on how he/she may properly use the patient interface and/or the pressure support system. The term "personalized" is used herein to clarify that the advices do not just include general information, but information that is individually adapted to the specific patient currently using the patient interface and/or the pressure support system.

The term "virtual model" of the head of the patient (or at least parts of it) refers to a two-dimensional (2D) or three-dimensional (3D) model of the patient's head (or at least parts of it). This virtual model may e.g. be obtained by means of a 2D or 3D scanning apparatus that reproduces the shape and size of the head of the patient in virtual form.

The "technical data" include information on the design and functionality of the patient interface and/or of the pressure support system. The technical data may, for example, include information on the shape, size and geometry of the patient interface. In particular, the technical data may include information on how to generally attach the patient interface to a head of a patient. It may include information about the size, shape and functionality of the headgear of the patient interface, e.g. information on how many headgear straps the headgear includes and to which parts of the head these headgear straps have to be attached. It may also include information on the material and material properties (e.g. elasticity and/or weight of the material of the headgear). The technical data may furthermore include information on the functionality of the pressure support system and information on the settings that are applicable by the pressure generator (the PAP therapy device). The technical data may also include information on the size, shape, geometry and functionality of the one or more conduits connecting the pressure generator to the patient interface.

The "usage data" include information on how the patient is using the patient interface. These data may include one or more images or a video of the patient wearing the patient interface. Hence, such images or videos show how the patient is using the patient interface, i.e. the way the patient interface is donned to the head of the patient. The usage data may also include sounds that are recorded, e.g. by means of a microphone, while the patient is wearing the patient interface and while the PAP therapy is ongoing. Still further, the usage data may include distances measured by means of a distance sensor, said distances exemplarily including a distance between the system and the patient's head, a distance between the patient's head and the patient interface and/or distances between the patient's head and a distinctive component of the pressure support system. The usage data may also include signals of other sensors, e.g. sensor that are arranged in the patient interface or the pressure generator, as this will be explained in more detail further below.

The "receiving unit" and the "advice unit" may be implemented as hardware and/or software modules. The receiving unit may e.g. comprise a data interface, such as an USB-interface, a Bluetooth®-interface, an infrared data interface, an Ethernet interface, or any other type of data interface. The advice unit may be implemented as a microchip or processor.

In summary, the presented system may be used as an interactive manual that helps inexperienced, but also experienced users (patients) to correctly handle a patient interface and to correctly operate a pressure support system. The advice generated by the presented system may, for example, tell the patient how to correctly tighten the straps of the headgear and explaining the procedure that involves several steps to tighten the headgear straps. This advice will be adapted to the individual situation of the patient using the presented system. The system may also generate an advice list including instructions as to how to adjust the headgear straps to achieve a more comfortable, uniform pressure between the patient interface and the patient's face. The generated advice may also explain the patient how to correctly set the PAP device, i.e. which mode of operation he/she may select in order to achieve the best possible therapeutic results for him/her personally.

In order to generate the personalized advice the system makes use of a virtual model of the patient's head as well as of the above-mentioned technical data and the usage data. The advice unit may be configured to determine an optimal setting of the patient interface and/or of the pressure support system based on a comparison of the virtual model of the patient's head with the technical data. In other words, the information on the technical design and functionality of the patient interface (technical data) may be compared with a virtual 2D or 3D model of the patient's head. The technical data may also include a virtual 3D model of the patient interface, such that the afore-mentioned comparison includes a virtual attachment of the 3D model of the patient interface to the 3D model of the patient's head. This comparison may result in an "optimal setting". This optimal setting may include information how the patient interface is optimally attached/donned to the head of the patient, taking the individual shape and size of the patient's head into account. The optimal setting may e.g. include the settings of the headgear straps that lead to optimal comfort and function, i.e. information how strong the headgear straps should be tightened and where the headgear straps should be positioned for the individual patient.

The advice unit will then generate the personalized advice based on the determined optimal setting and the usage data. The advice unit may, for example, compare the determined optimal setting with the current setting of the patient interface included in the usage data in order to determine an advice for the patient how he/she may modify the position and/or settings of the patient interface to get from the current setting to the optimal setting. The advice unit may be either configured to provide such an advice on demand of the patient, or having identified triggers indicating it might be beneficial for the patient to output an advice. This will be explained in detail further below.

The system may further comprise at least one of the following devices being coupled to the receiving unit:

a camera for capturing at least one image of the patient with or without the patient interface;

a microphone, in particular a beam-formed microphone, for recording a sound during usage of the patient interface and/or the pressure support system by the patient; and a distance sensor for measuring a distance between the system or any components thereof and the head of the patient, a distance between the patient's head and the patient interface, a distance between the patient's head and a distinctive component of the pressure support system and/or a distance between distinctive components of the pressure support system;

wherein the usage data include said at least one image, said sound and/or at least one of said distances.

According to a first embodiment, the system may comprise:

a camera for capturing at least one image of the patient wearing the patient interface, wherein the camera is coupled to the receiving unit; and an image analysis unit for identifying within the at least one image a first reference location on the head of the patient and a second reference location on the patient interface or components thereof, wherein the image analysis unit is further configured to determine an orientation and/or position of the patient interface relative to the head of the patient based on the first and second reference location, and wherein the advice unit is configured to generate the personalized advice based on the virtual model, the technical data and the usage data, wherein the usage data include said determined orientation and/or position of the patient interface.

The patient may thus don the patient interface to his/her head and then use the camera to image him-/herself wearing the patient interface. Instead of taking only one image, the patient may also take several images or a video using the camera. The image analysis unit is configured to identify at least one reference location on the head of the patient (herein denoted as first reference location) and at least one reference location on the patient interface or components thereof (herein denoted as second reference location). These reference locations indicate specific features in the image that may be easily observed by means of an image analysis technique. The terms "first" and "second" are herein only used to differentiate between the reference locations on the head of the patient and the reference locations on the patient interface, but shall not imply a quantity or a chronological order. Typical reference locations that could be identified by means of the image analysis unit are the nose, the mouth and/or the eyes of the patient as well as characteristic elements of the patient interface, e.g. the mask shell, the mask cushion, the headgear straps or the connection points of the headgear straps to the mask shell. Using these reference locations the image analysis unit may be configured to determine an orientation and/or position of the patient interface relative the head of the patient. The advice unit may then take as inputs: (i) the virtual model of the patient's head, (ii) information pertaining to the specific patient interface (e.g. guidelines on the best position and/or strap configuration) (the "technical data"), (iii) the first reference locations, (iv) the second reference locations (the first and second reference location in this case forming part of the "usage data"). From these inputs the advice unit may determine whether the placement of the patient interface is adequate (i.e. conforms with the optimal setting of the patient interface), or not. If the placement is not adequate, the advice unit may be configured to determine the difference between the current setting (orientation and/or position) of the patient interface to the optimal setting of the patient interface and to generate corresponding adjustment instructions (the "personalized advice") on how to improve the current use of the patient interface. The advice unit may, for example, generate a list of instructions as how to adjust the headgear straps to achieve a better, more uniform pressure between the patient interface and the patient's head.

According to a further embodiment, the system may comprise:

a camera for capturing at least one image of the patient, wherein the camera is coupled to the receiving unit; and an image analysis unit for identifying skin irritations on the head of the patient within the at least one image, and wherein the advice unit is configured to generate the personalized advice based on the virtual model, the technical data and the usage data, wherein the usage data include information on said identified skin irritations and their position.

In this embodiment the patient may use the camera to capture an image or a video of him-/herself after the patient interface has been worn for a certain amount of time (e.g. after one night). The image analysis unit may in this case be configured to identify skin irritations on the patient's head, such as regions of reddened skin, within the at least one image. This may, for example, be done by analyzing the color values of each pixel within the at least one image. The skin irritations identified therewith may give an indication of regions of excessive pressure caused by a patient interface that is donned overly tight to the patient's head. The advice unit may then take as inputs: (i) the identified positions of the skin irritations obtained by the image analysis unit (these data form part of the "usage data"), (ii) the virtual model of the patient's head, and (iii) information pertaining to the design of the patient interface (the "technical data"). By comparing these data with each other as explained before, the advice unit may then produce a list of instructions as how to adjust the patient interface to achieve a more comfortable, uniform pressure distribution between the mask and the patient's head. The personalized advice may, for example, include information for the patient how the straps of the headgear should be adjusted in order to bring the patient interface in its optimal setting for the particular patient.

According to a further embodiment, the system may comprise:

a camera for capturing at least one image of the patient wearing the patient interface, wherein the camera is coupled to the receiving unit; and an image analysis unit for identifying within the at least one image a position, shape and/or colour of a visual indicator provided on the patient interface, and wherein the advice unit is configured to generate the personalized advice based on the virtual model, the technical data and the usage data, wherein the usage data include said position, shape and/or colour of the visual indicator.

The difference to the above-mentioned embodiment, in which several reference locations on the patient's head and on the patient interface were determined by the image analysis unit, is only that the reference locations may herein be identified by visual indicators provided on the patient interface. These visual indicators may help to identify the current setting of the patient interface. The visual indicators may comprise one or more landmarks that may be identified in an electronic way by means of the image analysis unit. Instead of landmarks the visual indicator could also be represented by a headgear strap or other component of the patient interface that is configured to change its color depending on the tensile force that is applied to it. This color change may thus be used as an indication for the tensile force applied in each of the identified patient interface components. A still further example of such a visual indicator is a display arranged on the patient interface which shows alphanumeric information indicating the position of the patient interface and/or the tensile force applied in the different headgear straps.

According to a further embodiment, the system may comprise:

a microphone, in particular a beam-formed microphone, for recording a sound during usage of the patient interface and/or the pressure support system by the patient, wherein the microphone is coupled to the receiving unit;

a sound analysis unit for determining a characteristic and/or location of said sound, wherein the advice unit is configured to generate the personalized advice based on the virtual model, the technical data and the usage data, wherein the usage data include the determined characteristic and/or location of said sound.

This embodiment may be used to detect a leak between the patient interface and the patient's head that might occur due to a misalignment of the patient interface. A beam-formed microphone may be configured to detect the location of the leak whilst being held in a stationary position in front of a known part of the patient's head (e.g. the nose). The sound analysis unit may analyze the sound signals received from the beam-formed microphone in order to determine the magnitude of the leak by using a combination of the extent (loudness) of the recorded sound and a known distance between the beam-formed microphone and the known part of the patient's head. The distance between the microphone and the known part of the patient's head may be determined by means of a distance sensor that is configured to measure the distance between the beam-formed microphone and the patient's head. The system may thus also comprise such a distance sensor.

Instead of using a beam-formed microphone, a "regular" microphone may be used that is moved in a loop fully circumnavigating the patient interface. The system may in this case also comprise an inertial sensor that is configured to track the position and/or orientation of the apparatus/system relative to the patient's head. The signals of the microphone and the signals of the inertial sensor may thus be used to determine the position and magnitude of the leak.

In both cases (usage of a beam-formed microphone and usage of a "regular" microphone together with a distance or inertial sensor) the advice unit takes as inputs: (i) the information gained by the beam-formed microphone or the "regular" microphone which were quantified by the image analysis unit as explained before (the "usage data"), (ii) the virtual model of the patient's head, and (iii) information pertaining to the technical design and functionality of the patient interface (the "technical data"). From these inputs the advice unit may calculate a list of instructions (the "personalized advice") as how to adjust the patient interface to remove the leak.

According to a further embodiment, the receiving unit is further configured to receive patient interface signals from a sensor arranged at the patient interface as a part of the usage data, wherein said patient interface signals include: (i) information on a gas parameter of the flow of breathable gas provided to the patient via the patient interface, (ii) information on a pressure with which the patient interface is donned to the head of the patient, and/or (iii) information on a tensile force occurring within a headgear of the patient interface, and wherein the advice unit is configured to generate the personalized advice based on the virtual model, the technical data and the usage data, wherein the usage data include the patient interface signals.

In other words, the usage data may include signals (herein denoted as patient interface signals) which are recorded by a sensor that is arranged at the patient interface. Such a sensor may, for example, sense a gas pressure occurring within the patient interface in order to identify any leakages. A sensor could also comprise a contact sensor that is configured to measure the contact pressure occurring at the interface between the patient interface and the patient's head. This sensor may thus sense whether the patient interface is arranged too tight on the patient's head. A still further example is a sensor that is configured to measure the tensile force occurring within the headgear or certain straps of the headgear of the patient interface. The above-mentioned patient interface signals may be used to increase the accuracy of the usage data. In this case, the advice unit may take as inputs: (i) the information gained from the sensor arranged at the patient interface (as part of the "usage data"), (ii) the virtual model of the patient's head, and (iii) information pertaining to the technical design and functionality of the patient interface (the "technical data").

The technical data may either be received from a storage unit that is arranged remote from an apparatus of the system, wherein said apparatus is connected to the receiving unit by means of a wireless or hard-wired connection. However, the technical data may also be stored in a database that is comprised within the same apparatus of the system that also comprises the receiving unit, the advice unit and one or more of the other sensor mentioned above. According to an embodiment, the system comprises a database for storing the technical data, wherein the technical data include one or more of (i) a geometry and/or size of the patient interface, (ii) a number, size, shape and/or material of headgear straps of the patient interface, and (iii) available settings of the pressure support system.

The virtual model of the patient's head may also be stored in a remotely arranged database or in a database that is comprised in the apparatus. According to an embodiment, the system may comprise a user database for storing user data, wherein the user data include the virtual model of the head of the patient and one or more of (i) physical data of the patient, (ii) medical data of the patient, and (iii) personal preferences of the patient, wherein the advice unit is configured to generate the personalized advice based on the user data, the technical data and the usage data.

This user database may thus not only be used to store the virtual model of the patient's head, but also for storing several other personal parameters of the patient such as physical data, medical data and/or personal preferences. These data may be used by the advice unit to further individualize the generated advice to the specific patient. The "physical data" may include information on the age, the height and/or the weight of the patient. The "medical data" may include information on a type of disease the patient suffers from and/or a type of therapy, e.g. the type of PAP therapy, the patient has received in the past. The "personal preferences" may include information on the preferences regarding the usage of a patient interface and/or a pressure support system. These personal preferences may, for example, include information about the type of patient interface (nasal mask, oral mask or full face mask) the patient prefers and/or information how the patient has set the device parameters of the pressure generator of the pressure support system in the past. All these data may be used by the advice unit in addition to the technical data, the virtual model of the patient and the usage data to generate the personalized advice.

According to a further embodiment, the system further comprises:

a usage data analysis unit for determining a malfunction and/or misalignment of the patient interface and/or of the pressure support system based on the usage data; and an output unit for outputting the personalized advice;

wherein the advice unit is configured to generate and output the personalized advice via the output unit if the usage data analysis unit determines a malfunction and/or misalignment of the patient interface.

This usage data analysis unit may comprise the image analysis unit and/or the sound analysis unit mentioned before. The usage data analysis unit may thus determine a malfunction and/or misalignment of the patient interface and/or of the pressure support system based on signals provided by a camera, a microphone, a beam-formed microphone, a distance sensor and/or a sensor that is arranged at the patient interface. It should be clear that, although these different types of sensors have been described with respect to separate embodiments, these sensors may also be combined, such that the usage data analysis unit receives the signals of some or all of these sensors. It should be also clear that the more sensors are provided, the better may the malfunction and/or misalignment be determined, and the better is the personalized advice generated by the advice unit.

If the advice unit is configured to generate and output the personalized advice in case the usage data analysis unit determined a malfunction and/or misalignment of the patent interface, the personalized advice is so to say output in an automatic manner, triggered by the usage data analysis unit. In other words, the patient will automatically receive an advice as soon as a malfunction and/or misalignment of the patient interface is detected. The advice unit may, for example, be configured to generate and output the personalized advice if the sound recorded by the microphone is above a certain threshold level. The advice unit may similarly be configured to generate and output the personalized advice if the patient interface signals measured with the sensor arranged at the patient interface includes any characteristic feature that is above a certain threshold level and/or indicative of a malfunction and/or misalignment.

The above-mentioned output unit may be realized in several ways, e.g. as a display showing the personalized advice in written or graphical form, or as a loudspeaker giving out the personalized advice in audible form or speech form.

Instead of automatically triggering the output of the personalized advice, the personalized advice could also be generated and output in response to a user input, e.g. a user actively requesting an advice by activating a button or an item in a user interface menu. In this case the system preferably comprises: an output unit for outputting the personalized advice, and an input unit which is configured to generate an advice request signal upon activation of the input unit by the patient, wherein the advice unit is configured to generate and output the personalized advice via the output unit upon receiving the advice request signal.

According to a further embodiment, the system comprises a display for displaying an image of the patient interface and/or of the pressure support system, wherein the display is further configured to virtually overlay the personalized advice on said image. The system may e.g. make use of an augmented reality technique that displays the personalized advice on the display in text form or graphical form overlaid on the image or video that the patient takes from him-/herself wearing the patient interface. On the other hand, the display could also be configured to show a static image of the patient interface and virtually overlay the personalized advice. This may facilitate to understand the personalized advice in an easy, realistic and quick manner.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
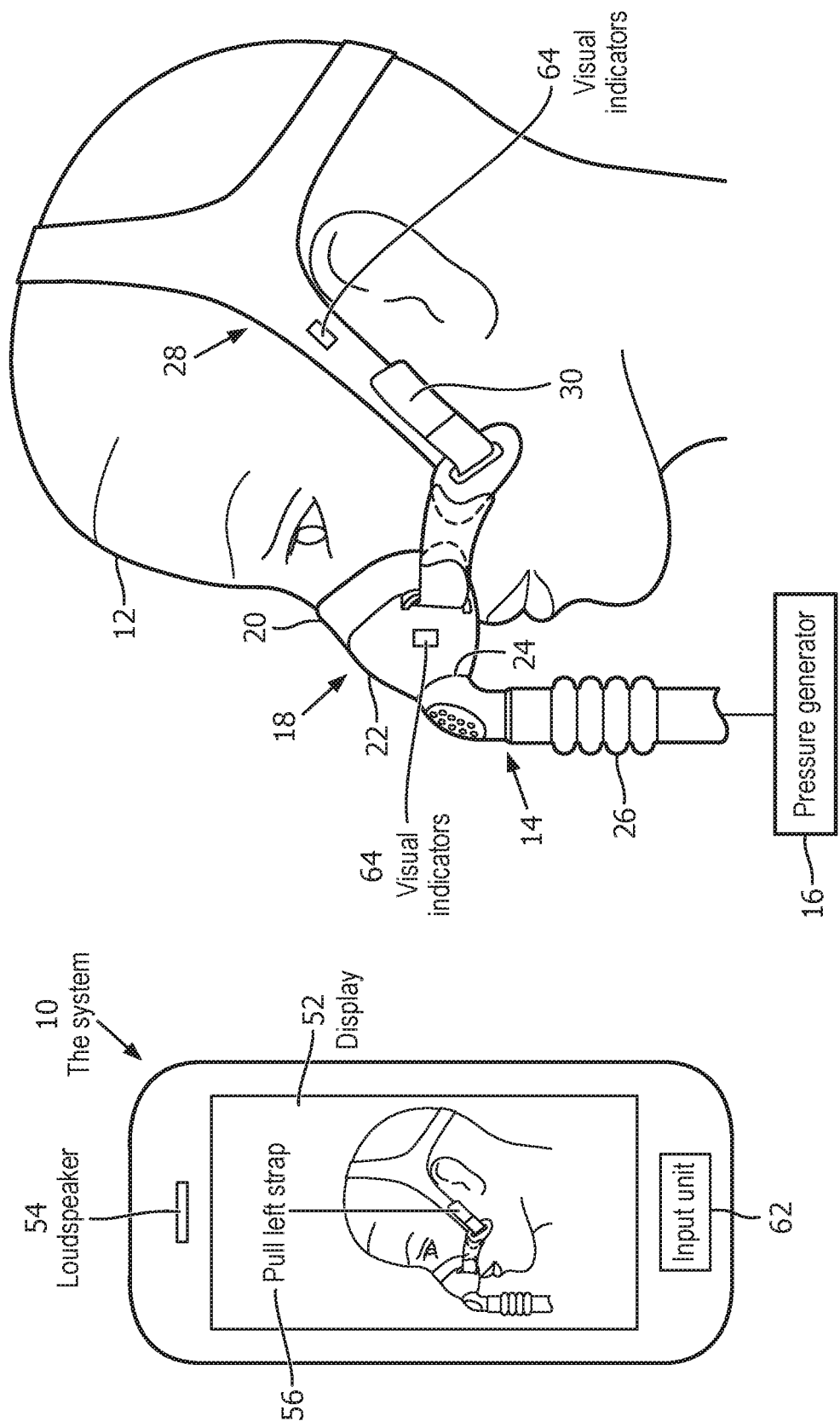
FIG. 1 shows a first exemplary embodiment of a system according to the present invention.

FIGS. 1-4 show two exemplary embodiments of a system according to the present invention. The system is therein in its entirety denoted by reference numeral 10.

Figure 2:
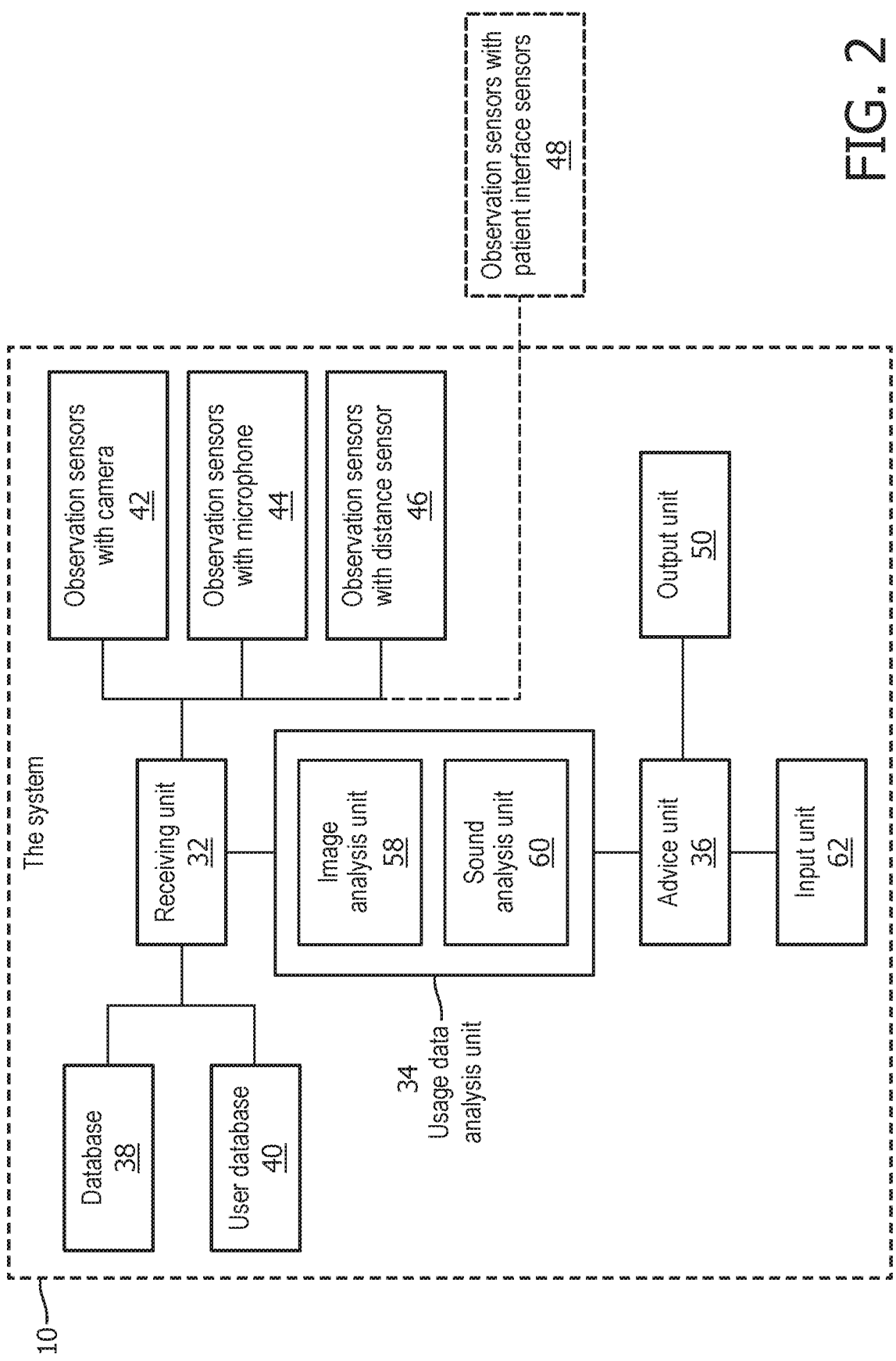
FIG. 2 shows a schematic block diagram illustrating the components of the system according to the first exemplary embodiment shown in FIG. 1.

FIGS. 1 and 2 show a first exemplary embodiment of the system 10. The system 10 is configured to provide a patient 12 with a personalized advice relating to a use of a pressure support system 14. Such a pressure support system 14 typically includes a pressure generator 16 and a patient interface 18. The system so to say provides the patient 12 with an interactive manual that advices/instructs the patient 12 how to use the pressure support system 14 and its components in a correct way. The system 10 may provide the patient 12 with interactive explanations helping the patient 12 to improve the use of the pressure support system 14 and to correct any malfunctions. These explanations/instructions (herein denoted as personalized advices) include information that are individually adapted to the patient 12. The system 10 thereto observes the patient 12 while using the pressure support system 14 and generates the personalized advices based on these observations, such that the personalized advices are specifically adapted to the patient 12 him-/herself and to the current situations how the patient 12 is using the pressure support system 14. The details on how these personalized advices are generated will be explained further below.

Before explaining the details of the system 10, the general components of a pressure support system 14 shall be explained. In the embodiment shown in FIG. 1, the patient interface 18 is designed as a nose mask covering the nose of the patient 12. Other patient interfaces 18 may be designed as nasal pillows, mouth masks, full-face masks or as total face masks without leaving the scope of the present invention. Patient interfaces 18 of this type usually comprise a cushion element 20 and a mask shell 22. The cushion element 20 is designed to contact the face of the patient 12 and to provide an airtight seal at the interface between the patient's face and the patient interface 18. The cushion element 20 is usually comprised of a soft material, like silicon or any other rubber or suitable elastic material. The mask shell 22 provides a flexible, semi-rigid or rigid support structure for holding the cushion element 20. The mask shell 22 may either be releasably or fixedly connected to the cushion element 20. The cushion element 20 and the mask shell 22 thus together form a cavity which is in the case illustrated in FIG. 1 designed to receive the nose of the patient 12. The cushion element 20 and the mask shell 22 together form a sealing portion of the patient interface 18. It shall be noted that the sealing portion does not necessarily have to be formed from two separate parts (the cushion element 20 and the mask shell 22), since the cushion element 20 and the mask shell 22 may also be realized as one integral part.

On a side directing away from the patient's face, the mask shell 22 preferably comprises a connector 24. Via this connector 24 the patient interface 18 may be connected to a hose or conduit 26 via which the personalized flow of breathable gas is transferred from the pressure generator 16 to the patient interface 18. The patient interface 18 usually further comprises a headgear 28 that may be e.g. connected to the mask shell 22. This headgear 28 preferably includes one or more headgear straps 30 for donning the mask shell 22 and the cushion element 20 to the patient's face. In other alternative variations the headgear 28 may additionally comprise a forehead support including a forehead cushion (not shown). Such a forehead support allows stabilizing the patient interface 18 while being donned to the patient's face and thereby reduces the pressure that is exerted onto the patient's nose during use.

As already mentioned above, the system 10 according to the present invention shall support especially inexperienced patients 12 to correctly use the patient interface 18 and the other components of the pressure support system 14. The advices provided by the system 10 are generated in a personalized manner, i.e. personalized to the patient's physical parameters (e.g. to the face and/or head shape and size of the patient 12) and also tailored to the specific pressure support system 14 in use as well as to the current conditions and user settings or configurations of the pressure support system 14 and/or the patient interface 18 (e.g. tailored to the current arrangement of the patient interface 18 on the patient's face or to the current arrangement of the headgear straps 30 on the patient's head). The system thereto makes use of several sensors that observe the patient 12 and provide usage data including information on how the patient 12 is using the patient interface 18 and/or the pressure support system 14.

In the exemplary embodiment shown in FIG. 1 the system 10 comprises a single apparatus 10 that is realized as a mobile device, e.g. as a mobile telephone. However, the system 10 could also be realized as another mobile device, such as a tablet PC or a laptop.

The components of the system according to the first embodiment are schematically shown in FIG. 2. The system 10 may comprise a receiving unit 32, a usage data analysis unit 34 and an advice unit 36. Still further, the system 10 may comprise a database 38 for storing technical data relating to the pressure support system 14 and its components (e.g. information on the geometry and/or size of the patient interface 18, a number, size, shape and/or material of the headgear straps 30 of the patient interface 18, and available settings of the pressure generator 16). The system 10 may also comprise a user database 40 for storing user data, e.g. data including information on the patient's physical parameters (e.g. a virtual 3D model of the patient's head and/or information on a face shape, a head shape, a face size, a head size, a weight or a height of the patient 12). Both databases 38, 40 may alternatively also be realized as a common database. The databases 38, 40 may, e.g. include a hard drive or any other electronic storage means. It shall be also noted that even though the above-mentioned units are in FIGS. 1 and 2 shown to be comprised in one and the same apparatus, one or more of the receiving unit 32, the usage data analysis unit 34, the advice unit 36, the database 38, and the user database 40 may also be arranged in a separate apparatus that is remotely located from the remaining apparatus of the presented system.

The receiving unit 32 is preferably realized as a data interface that is configured to receive and collect all data and to transfer these data to the advice unit 36 for further processing. The receiving unit 32 preferably receives a virtual 3D model of the patient's head and transfers it to the advice unit 36. Such a 3D model of the patient's head may e.g. be acquired by means of a 3D scan of the patient 12 that is performed in advance to the usage of the system 10. However, the system may also comprise such a 3D scanner, so that the 3D model of the patient's head may be generated by the patient 12 him-/herself in a life session. If the 3D virtual model of the patient's head is pre-acquired, it may be stored in the user database 40.

The receiving unit 32 is further configured to receive the technical data relating to the technical design and functionality of the patient interface 18 and/or of the pressure support system 14 from the database 38, wherein the receiving unit 32 is further configured to transfer these data to the advice unit 36.

The receiving unit 32 is further configured to receive usage data including information on how the patient 12 is currently using the patient interface 18 and/or the pressure support system 14. These usage data may be acquired by means of several observation sensors 42, 44, 46 and 48 which observe the patient 12 while he/she is wearing the patient interface 18. These observation sensors 42-48 may include one or more of a camera 42, a microphone 44, a distance sensor 46 and one or more patient interface sensors 48. In the exemplary example shown in FIGS. 1 and 2, the camera 42, the microphone 44 and the distance sensor 46 are included in the apparatus, while the one or more patient interface sensors 48 are arranged remote from the apparatus 10 at the patient interface 18 or any components thereof. All observation sensors 42-48 may be connected to the receiving unit 32 either by means of a wireless connection or by means of a hard-wired connection.

The advice unit 36 is configured to generate the personalized advice on how to improve the current use of the patient interface 18 and/or the pressure support system 14 based on the virtual 3D model of the user's head received from the user database 40, the technical data received from the database 38 as well as based on the usage data received from the one or more observation sensors 42-48. The personalized advice generated by means of the advice unit 36 may be output to the patient 12 via an output unit 50. The output unit 50 preferably includes a display 52 with which the apparatus 10 is equipped. The output unit 50 may furthermore comprise a loudspeaker 54 for giving out the personalized advice in audible form.

The advice unit 36 may be realized as software and/or hardware. The advice unit 36 may, for example, comprise a processor including one or more program modules which are configured to carry out an advice adapting algorithm. These program modules may e.g. be realized as a software application which is stored in the apparatus 10. The advice adapting algorithm calculates the personalized advice that helps the patient to improve the use of the pressure support system 14 and its components based on the virtual 3D model, the technical data and the usage data. The advice unit 36 may be configured to determine an optimal setting of the patient interface 18 and/or the pressure support system 14 based on a comparison of the virtual 3D model of the patient's head received from the user database 40 with the technical data received from the database 38. The advice unit 36 may then compare the usage data received from the one or more observation sensors 42-48 with the determined optimal setting in order to generate the personalized advice. In other words, the advice unit 36 may be configured to analyse the usage data received from the one or more observation sensors 42-48 in order to check whether these usage data indicate a setting of the patient interface 18 that deviates or conforms with the optimal setting for the patient 12. If the current settings included in the usage data deviate from the optimal settings determined based on the virtual 3D model of the patient's head and the technical data of the patient interface 18, the advice unit 36 generates a personal advice that shows the patient 12 how he/she may correct the settings of the patient interface 18. An exemplary advice may include an image displayed on the display 52, wherein the image shows the patient wearing the patient interface 18 including a written advice 56 which is virtually overlaid on said image. The personalized advice 56 may e.g. tell the user to pull the left strap 30 of the headgear 28 by e.g. 10 mm. The personalized advice 56 may also include one or more graphical symbol and/or an audible message output via the loudspeaker 54. The personalized advice 56 may also be in the form of a process, i.e. a number of steps each with a parameterized instruction.

Different applications of the presented system are exemplarily described in the following:

The patient 12 may don the patient interface 18 to his/her face and then use the camera 42 of the system 10 to image him-/herself wearing the patient interface 18. The patient 12 may either take a single image or multiple images forming a video. These one or more images are received by the receiving unit 32 and may then be transferred to an image analysis unit 58 which may form part of the usage data analysis unit 34. The image analysis unit 58 may be configured to identify features in the one or more images delivered by the camera 42. The image analysis unit 58 may e.g. be configured to identify a first reference location on the head of the patient 12 and at least one second reference location on the patient interface 18 in order to determine an orientation and/or position of the patient interface 18 relative to the head of the patient 12. The image analysis unit 58 may thereto comprise an image matching algorithm that is used to identify distinctive features on the patient interface 18 and the head of the patient 12. This image matching algorithm may e.g. identify the mask shell 22 and/or the headgear straps 30 as well as objects in the patient's face, such as the nose, the mouth and/or the eyes of the patient 12. In order to facilitate the identification of the reference locations, the patient interface may optionally comprise one or more visual indicators 64. The image analysis unit 58 may e.g. comprise one or more program modules that form part of the software application which also carries out the functions of the advice unit 36. It shall be noted that the user data analysis unit 34 and the advice unit 36 are herein only separated for the purpose of explanation, but may in reality be realized in the same software and/or hardware unit. In the exemplarily described application the advice unit 36 will use the following inputs for calculating the personalized advice: (i) the orientation and/or position of the patient interface 18 relative to the patient's head which was determined by means of the image analysis unit 58, (ii) the virtual 3D model of the patient 12 received from the user database 40, and (iii) the technical data received from the database 38. The advice unit 36 may e.g. be configured to compare the orientation and/or position of the patient interface 18 determined by the image analysis unit 58 with an optimal setting of the patient interface 18 determined based on the 3D model of the patient 12 and the technical data of the patient interface 18.

Another exemplary application of the system 10 includes the usage of the microphone 44. This microphone 44 may be used to detect leaks occuring at the interface between the patient interface 18 and the head of the patient 12. The microphone 44 may e.g. include a beam-formed microphone array that is configured to detect a location of such a leak. The patient 12 may hold the apparatus 10 including the microphone 44 at a prescribed position relative to his/her head. Alternatively, the patient 12 may move the apparatus 10 along a prescribed route around his/her head, e.g. moving the apparatus in a loop fully circumnavigating the head of the patient 12 and/or the patient interface 18. The apparatus 10 may include an inertial or position sensor that tracks the position at each point of said route. Alternatively or additionally, the distance sensor 46 may be used to determine the distance between the microphone 44 and the patient's head during said movement. The distance sensor 46 may e.g. comprise an optical sensor, such as a laser sensor, or a radar-based sensor. The advice unit 36 may be configured to generate an advice to the patient 12 how he/she has to hold and/or move the apparatus 10 in this case. These advices may e.g. include one or more direction advices that are displayed on the display 52. The sounds recorded by the microphone 44 during the usage of the pressure support system 14 may then be transferred to a sound analysis unit 60 that may form part of the usage data analysis unit 34, similar as the afore-mentioned image analysis unit 58. The sound analysis unit 60 may be configured to determine a characteristic and/or location of said sounds. The sound analysis unit 60 may also use the signals received from the distance sensor 46 and/or the inertial/position sensor (not shown). Based on these information the sound analysis unit 60 may e.g. determine a magnitude and a location of a leak occurring at the interface between the patient interface 18 and the head of the patient 12. The advice unit 36 may then generate a personalized advice helping the patient 12 to remove the detected leak. The advice unit 36 may calculate this advice based on the following input information: (i) the information on the magnitude and/or position of the leak determined by means of the sound analysis unit 60, (ii) the virtual 3D model of the patient's head received from the user database 40, and (iii) the technical data received from the database 38. Similar as according to the first example (making use of the camera 42), the advice unit 36 may finally output the personalized advice 56 via the display 52 and/or the loudspeaker 54. An exemplary personalized advice 56 may include the instruction to move the patient interface 18 5 mm to the right and/or to pull the left headgear strap 30 through the clasp by 10 mm.

A third exemplary application of the presented system 10 may relate to a reduction of discomfort due to an incorrect placement of the patient interface 18. The patient 12 may thereto use the camera 42 to take one or more images of him-/herself after he/she has worn the patient interface 18 for a certain amount of time (e.g. for one night). The one or more images taken by the camera 42 should in this case only include the face of the patient 12 without the patient interface 18. These images are received by the receiving unit 32 and transferred to the image analysis unit 58. The image analysis unit 58 may be configured to identify skin irritations, such as a reddened skin, as well as their positions by means of an image analysis technique. The identified information on the magnitude and position of these skin irritations may be transferred to the advice unit 36. The advice unit 36 may then generate a personalized advice 56 including information on how the patient 12 may change the settings of the patient interface 18 and/or the pressure generator 16 in order to get (at least partly) rid of the skin irritations, i.e. in order to achieve a more comfortable setting. The advice unit 36 may base the calculations for this personalized advice 56 based on the following inputs: (i) the location and/or magnitude of the skin irritations as obtained by the image analysis unit 58, (ii) the 3D virtual model of the patient's head received from the user database 40, and (iii) the technical data received from the database 38.

In all three above-mentioned exemplary applications of the system 10, the generation of the personalized advice 56 may be optionally further refined based on the signals provided by the one or more patient interface sensors 48. These patient interface sensors 48 may deliver further usage data that allow a more accurate determination how to change the settings of the patient interface 18 and/or the pressure generator 16. The one or more patient interface sensors 48 may include the following sensor types: 1. a gas flow sensor which is arranged at or within the patient interface 18 and/or the hose 26 and configured to measure one or more gas parameters (e.g. pressure, temperature, humidity, etc.) of the flow of breathable gas provided to the patient 12; 2. an extensometer (e.g. a strain gauge) which is arranged at one of the headgear straps 30 or at the connection between the headgear straps 30 and the mask shell 22 and which is configured to measure a tensile stress or force occurring within the headgear straps 30; 3. a pressure or force sensor which is arranged within the cushion element 20 and which is configured to measure a pressure/force with which the patient interface 18 is donned to the patient's face.

The advice unit 36 may in all the above-mentioned applications be triggered in at least two different ways. According to a first alternative, the system 10 may comprise an input unit 62 which includes one or more input fields or buttons. If the patient 12 activates said input unit 62, the advice unit 36 will be triggered to generate the personalized advice 56 in the ways mentioned above. However, the advice unit 36 may, according to a second alternative, also be configured to generate and output the personalized advice in an automatic manner without the need of any user feedback. The advice unit 36 may be triggered by the user data analysis unit 34. In other words, the advice unit 36 may be configured to generate and output the personalized advice 56 via the output unit 50 if the usage data analysis unit 34 determines a malfunction and/or misalignment of the patient interface 18 and/or the pressure generator 16 observed by means of the one or more observation sensors 42-48. Exemplary triggers for the advice unit 36 could be: 1. an observed sound above a certain threshold detected by means of the sound analysis unit 60, 2. a misalignment of the patient interface 18 detected by means of the image analysis unit 58, 3. a skin irritation in the patient's face detected by means of the image analysis unit 58, 4. a too close arrangement of the pressure generator 16 relative to the patient's head detected by means of the image analysis unit 58, and 5. a gas parameter exceeding a certain threshold value detected by means of the one or more patient interface sensors 48.

Figure 3:
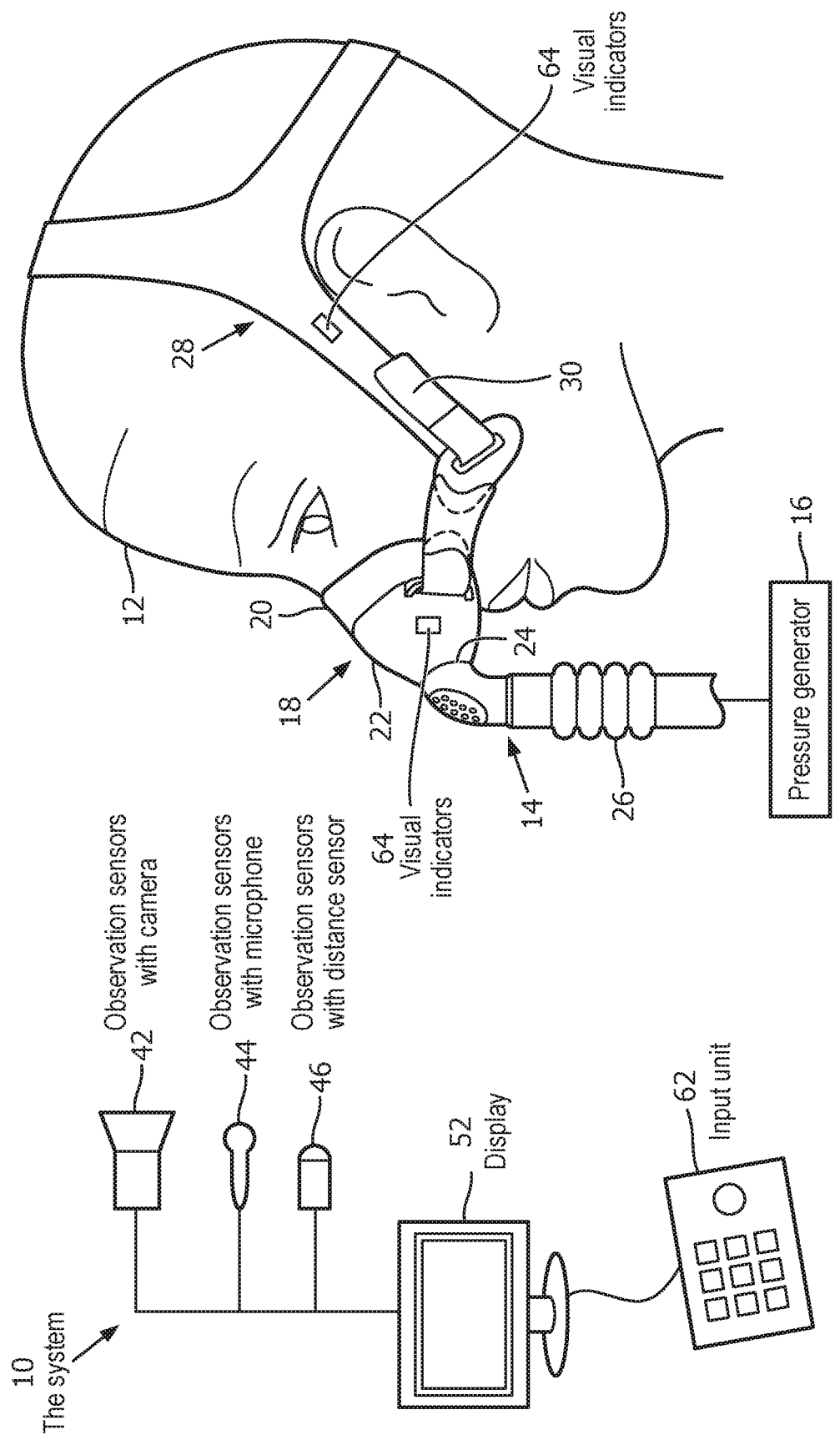
FIG. 3 shows a second exemplary embodiment of the system according to the present invention.
Figure 4:
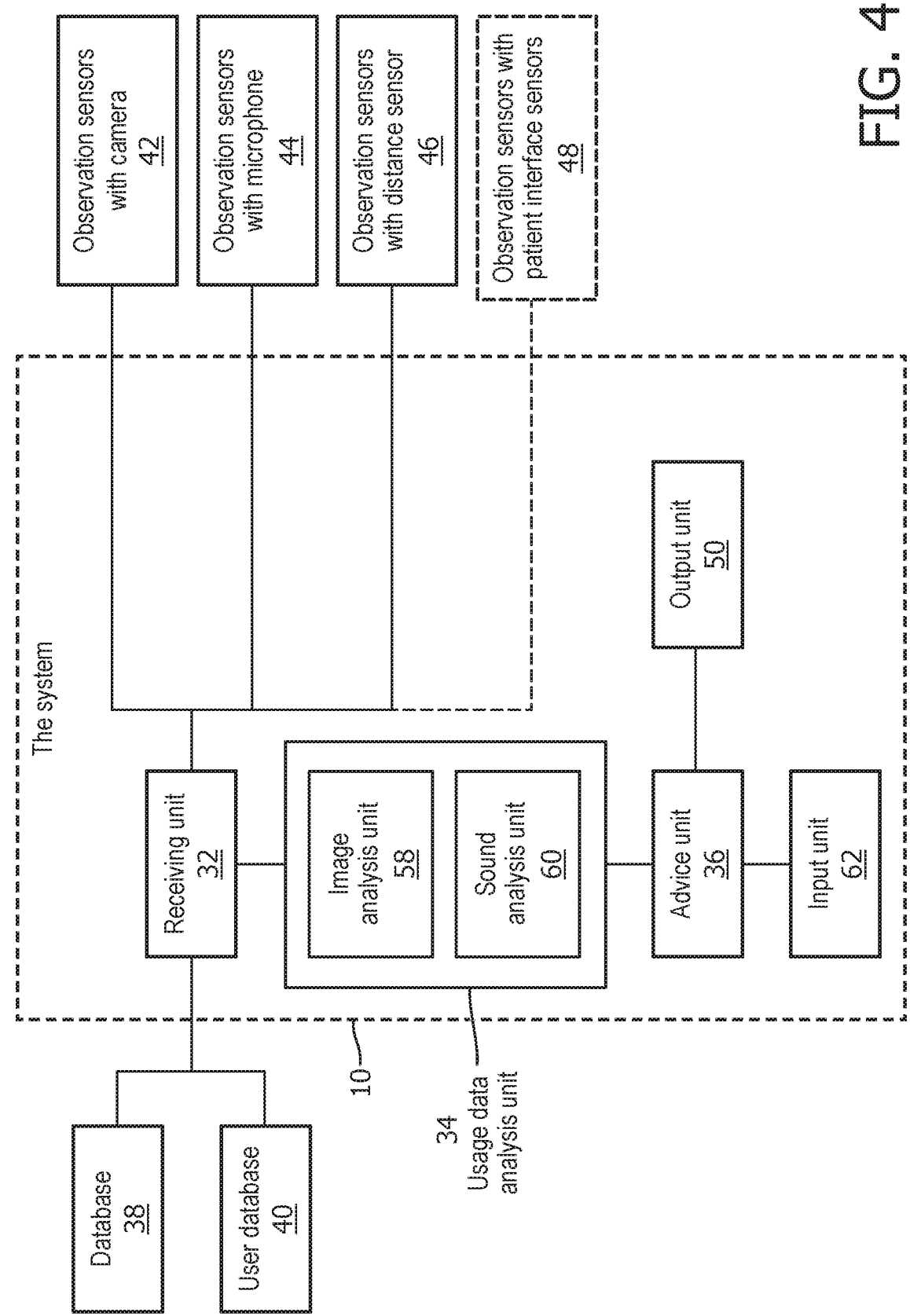
FIG. 4 shows a schematic block diagram illustrating the components of the second exemplary embodiment of the system shown in FIG. 3.

FIGS. 3 and 4 show a second exemplary embodiment of the system 10 according to the present invention. Same or similar components are therein denoted with the same reference numerals. The principle and function of the system 10 according to the second embodiment basically remains the same as explained before with reference to the first embodiment shown in FIGS. 1 and 2. The following thus only includes a short explanation of the differences. The system 10 according to the second embodiment does not include a mobile device, but as a stationary computing device. This stationary computing device may include the same hardware and/or software components 32, 34, 36, 50, 62 as explained before. However, the camera 42, the microphone 44, the distance sensor 46 and/or the one or more patient interface sensors 58 do not form part of the stationary computing device 10 itself, but may be arranged remote from the device 10. The observation sensors 42-48 are in this case connected to the device 10 by means of a wireless or hard-wired connection. The database 38 including the technical data as well as the user database 40 including the user data may also be remotely arranged from the device 10 and connected to the receiving unit 32 by means of a wireless or a hard-wired connection. The receiving unit 32 and the advice unit 36 may also be arranged in different devices. It is clear that the system according to both embodiments does not necessarily have to include all observation sensors 42-48, but may only include one or any arbitrary combination of these sensors 42-48.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for providing a patient with personalized advice relating to a use of a patient interface for providing a flow of breathable gas and/or to a use of a pressure support system comprising the patient interface, the system for providing a patient with the personalized advice comprising:
   a receiving unit configured for receiving a virtual model of at least a part of a head of the patient, technical data relating to a technical design and functionality of the patient interface and/or of the pressure support system, and usage data including information on how the patient is using the patient interface and/or the pressure support system; and
   an advice unit configured for generating the personalized advice on how to improve the use of the patient interface and/or of the pressure support system based on the virtual model, the technical data and the usage data, wherein the advice unit is configured to determine an optimal setting of the patient interface and/or of the pressure support system based on a comparison of the virtual model with the technical data, and wherein the advice unit is configured to generate the personalized advice based on the optimal setting and the usage data.

2. The system according to claim 1, further comprising at least one of the following devices being coupled to the receiving unit:
   a camera for capturing at least one image of the patient with or without the patient interface;
   a microphone for recording a sound during usage of the patient interface and/or the pressure support system by the patient; and
   a distance sensor for measuring a distance between the system and the head of the patient, a distance between the patient's head and the patient interface, a distance between the patient's head and a component of the pressure support system and/or a distance between components of the pressure support system;
   wherein the usage data include said at least one image, said sound and/or one of said distances.

3. The system according to claim 1, further comprising:
   a camera for capturing at least one image of the patient wearing the patient interface, wherein the camera is coupled to the receiving unit; and
   an image analysis unit for identifying within the at least one image a first reference location on the head of the patient and a second reference location on the patient interface or components thereof, wherein the image analysis unit is further configured to determine an orientation and/or position of the patient interface relative to the head of the patient based on the first and second reference location, and
   wherein the advice unit is configured to generate the personalized advice based on the virtual model, the technical data and the usage data, wherein the usage data include said determined orientation and/or position of the patient interface.

4. The system according to claim 1, further comprising:
   a camera for capturing at least one image of the patient, wherein the camera is coupled to the receiving unit; and
   an image analysis unit for identifying skin irritations on the head of the patient within the at least one image, and wherein the advice unit is configured to generate the personalized advice based on the virtual model, the technical data and the usage data, wherein the usage data include information on said identified skin irritations and their position.

5. The system according to claim 1, further comprising:
a camera for capturing at least one image of the patient wearing the patient interface (18), wherein the camera is coupled to the receiving unit; and
an image analysis unit for identifying within the at least one image a position, shape and/or colour of a visual indicator provided on the patient interface, and
wherein the advice unit is configured to generate the personalized advice based on the virtual model, the technical data and the usage data, wherein the usage data include said position, shape and/or colour of the visual indicator.

6. The system according to claim 1, further comprising:
microphone for recording a sound during usage of the patient interface and/or the pressure support system by the patient, wherein the microphone is coupled to the receiving unit;
a sound analysis unit for determining a characteristic and/or location of said sound,
wherein the advice unit is configured to generate the personalized advice based on the virtual model, the technical data and the usage data, wherein the usage data include the determined characteristic and/or location of said sound.

7. The system according to claim 1, wherein the receiving unit is further configured to receive patient interface signals from a sensor arranged at the patient interface as a part of the usage data, wherein said patient interface signals include: (i) information on a gas parameter of the flow of breathable gas provided to the patient via the patient interface, information on a pressure with which the patient interface is donned to the head of the patient, and/or information on a tensile force occurring within a headgear of the patient interface, and
wherein the advice unit is configured to generate the personalized advice based on the virtual model, the technical data and the usage data, wherein the usage data include the patient interface signals.

8. The system according to claim 1, further comprising a database for storing the technical data, wherein the technical data include one or more of a geometry and/or size of the patient interface, a number, size, shape and/or material of headgear straps of the patient interface, and available settings of the pressure support system.

9. The system according to claim 1, further comprising a user database for storing user data, wherein the user data include the virtual model of the head of the patient and one or more of physical data of the patient, medical data of the patient, and personal preferences of the patient,
wherein the advice unit is configured to generate the personalized advice based on the user data, the technical data and the usage data.

10. The system according to claim 1, further comprising:
a usage data analysis unit for determining a malfunction and/or misalignment of the patient interface and/or of the pressure support system based on the usage data; and
an output unit for outputting the personalized advice;
wherein the advice unit is configured to generate and output the personalized advice via the output unit if the usage data analysis unit determines a malfunction and/or misalignment of the patient interface and/or of the pressure support system (14).

11. The system according to claim 1, further comprising a display for displaying an image of the patient interface and/or of the pressure support system, wherein the display is further configured to virtually overlay the personalized advice on said image.

12. The system according to claim 1, wherein the system for providing the patient with personalized advice comprising the pressure support system, wherein the pressure support system comprising: a pressure generator for generating a flow of breathable gas and the patient interface for providing the flow of breathable gas to the patient.

13. A method of using a system according to claim 1, for providing a patient with personalized advice relating to a use of a patient interface for providing a flow of breathable gas and/or to a use of a pressure support system comprising such a patient interface, the method comprising the steps of:
receiving a virtual model of at least a part of a head of the patient, technical data relating to a technical design and functionality of the patient interface and/or of the pressure support system, and usage data including information on how the patient is using the patient interface (18) and/or the pressure support system; and
generating the personalized advice on how to improve the use of the patient interface and/or of the pressure support system based on the virtual model, the technical data and the usage data, wherein generating the personalized advice involves determining an optimal setting of the patient interface and/or of the pressure support system based on a comparison of the virtual model with the technical data, and generating the personalized advice based on the optimal setting and the usage data.

14. A non-transitory computer-readable medium having instructions for causing a computer to carry out the steps of the method as claimed in claim 13.

* * * * *